US006779385B2

(12) United States Patent
Belanger

(10) Patent No.: US 6,779,385 B2
(45) Date of Patent: Aug. 24, 2004

(54) METHOD AND DEVICE FOR MONITORING MOISTURE CONTENT OF AN IMMERSED SOLID DIELECTRIC MATERIAL

(76) Inventor: Michel Belanger, 160, rue des Émeraudes, Boischatel, QBC (CA), G0A 1H0

( * ) Notice: Subject to any disclaimer, the term of this patent is extended or adjusted under 35 U.S.C. 154(b) by 45 days.

(21) Appl. No.: 10/194,265

(22) Filed: Jul. 15, 2002

(65) Prior Publication Data

US 2004/0007052 A1 Jan. 15, 2004

(51) Int. Cl.[7] .............................................. G01N 33/38
(52) U.S. Cl. ......................................................... 73/73
(58) Field of Search ................................ 73/73, 74, 75; 324/686; 374/100

(56) References Cited

U.S. PATENT DOCUMENTS

| 3,768,006 | A |   | 10/1973 | Mueller |
|-----------|---|---|---------|---------|
| 3,961,246 | A |   | 6/1976  | Waterman et al. |
| 4,186,592 | A | * | 2/1980  | Eirich et al. .................... 73/73 |
| 4,272,986 | A | * | 6/1981  | Lowry et al. ................... 73/73 |
| 4,498,305 | A |   | 2/1985  | Bzdula |
| 4,599,809 | A | * | 7/1986  | Parkes .......................... 34/484 |
| 4,662,220 | A |   | 5/1987  | Laue ......................... 73/335.02 |
| 4,837,499 | A | * | 6/1989  | Scherer, III ................. 324/696 |
| 5,301,543 | A |   | 4/1994  | Reichert |
| 5,343,045 | A |   | 8/1994  | Gupta |
| 5,654,643 | A | * | 8/1997  | Bechtel et al. ............... 324/687 |

FOREIGN PATENT DOCUMENTS

| DE | 100 13 001 A1 | 9/2001 |
|----|---------------|--------|
| EP | 0 628 803 A2  | 12/1994 |

OTHER PUBLICATIONS

Oommen, T. V.; "On–line moisture sensing in transformers"; Proceedings of the 20th Conf.; Oct. 7, 1991, Boston, IEEE, pp. 236–240, ISBN 0–7803–0018–1 (XP 010044711).

Anonymous; "Method for monitoring moisture content in cellulosictransformer insulation based on dielectric response"; Mar. 1995, Hampshire, GB, vol. 371, No. 22; ISSN:0374–4353.

Ylikangas, I.; "Improved Maintenance for Transformers"; Vaisala News, No. 154, Sep. 2002, pp. 11–12; (XP 002259391).

Davydov et al.; "Moisture assessment in power transformers, Lessons Learned"; Vaisala News, No. 160, Sep. 26, 2002, pp. 18–21, (XP 002259392).

* cited by examiner

*Primary Examiner*—Hezron Williams
*Assistant Examiner*—Katina Wilson

(57) ABSTRACT

A method and device for monitoring moisture content level of a solid dielectric material, or paper, immersed in a dielectric fluid, or oil, both of which having respective moisture content, and known water solubility properties varying with temperature. The device includes a moisture detector and a temperature detector for measuring moisture content level and temperature level of the oil, respectively. A microprocessor, electrically connected to both the moisture and the temperature detectors, computes the moisture content level of the paper. The microprocessor has the known water solubility properties of the paper and the oil stored therein and processes the oil moisture content level and the oil temperature level so as to determine the paper moisture content level. The latter being displayed on a display connected to the microprocessor.

20 Claims, 4 Drawing Sheets

METHOD AND DEVICE FOR MONITORING MOISTURE CONTENT OF AN IMMERSED SOLID DIELECTRIC MATERIAL

TITLE OF THE INVENTION

Method and device for monitoring moisture content of an immersed solid dielectric material.

FIELD OF THE INVENTION

The present invention relates to the field of sensing devices and is more particularly concerned with a method and a device for monitoring the moisture content of a solid dielectric material immersed in a dielectric fluid.

BACKGROUND OF THE INVENTION

As it is well-known in the art of high voltage transformers, the moisture content of the paper insulation used to insulate the wires in the windings affects the insulation characteristic of the transformer, the higher the moisture content is the lower its insulating characteristic is. High moisture content reduces the electrical resistance of the insulation which promotes local heating, especially during emergency overloading of the transformer, and increases the occurrences of small discharges that tend to degrade even further the paper insulation. Therefore, high moisture content shortens the insulation life duration.

It is also well known that the moisture content generally increases over time, mainly due to paper aging, infiltration and inspection. This increase of moisture content in the paper insulation forces the transformer to have a decreasing overload capacity over time.

The moisture content level of the paper insulation can be evaluated and/or estimated through the measurement of the moisture content level of the oil in which the windings, including the paper insulation, is immersed in. It is relatively easy to measure the moisture content of the oil since a lot of such devices are available in the market. Once the oil moisture content is known it is somewhat tedious to go through the analysis process in order to estimate the paper moisture content in different locations of the transformer. Accordingly, in practice, no one ever does or sees the necessity to do such an analytical estimation.

U.S. Pat. No. 5,343,045 granted to Gupta on Aug. 30, 1994, discloses a method and device for measuring moisture content of an absorbent material such as paper insulation in transformers. The device directly measures the humidity/moisture level in the absorbent material using an optical technique. The technique requires an end of an optic fiber to be installed almost in contact with the absorbent material or paper insulation.

Since the device provides a local direct measurement, is preferably located at a critical area of the transformer. Such a critical area is not always easily accessible and may require a somewhat complex and expensive installation of the device on the transformer. Furthermore, the location of such a critical area is not really known for sure and changes with the transformer loading. In order to get a general overview of the paper moisture content in the different locations of the transformer, either a plurality of devices or a calculated estimation is required. Notwithstanding the fact that such a device may provide reliability problems over time, especially problems associated with the maintaining of a proper position of the optical probe in proximity to the absorbent material.

The drawbacks associated with the prior art devices is their inability to provide an operator/user with a constant monitoring of the moisture level of the paper insulation using relatively simple and well-known temperature and humidity sensors. Furthermore, the assessment of the paper moisture content for different locations in the transformer is never performed due to its complexity. Nevertheless, such an assessment could prove to be beneficial over time in order to significantly increase the lifetime of the transformers as well as their continuous use at a substantially higher maximum overload capacity compared to their usual derated overload capacity required to compensate for all of the unmonitored behaviors thereof, for safety reasons.

Accordingly, there is a real need for an improved method and device for monitoring the moisture level of an immersed solid dielectric material.

Furthermore, an oil dryer-filter connected to the transformer is generally used to extract water from the oil. When such a filter becomes saturated in water, its efficiency is considerably reduced, if not null, and could affect the overload capacity of the transformer until it is replaced or cleaned up. Although the oil filters are generally provided with a known water extraction capacity, they sometimes lose efficiency before reaching the latter, which is bad for the transformer.

Accordingly, there is a need for continuously monitoring the proper functioning of the oil dryer-filter during operation of the high power transformer.

SUMMARY OF THE INVENTION

It is therefore a general object of the present invention to provide an improved method and device for monitoring moisture content of a solid dielectric material immersed in a dielectric fluid.

An advantage of the present invention is that the method and/or device for monitoring moisture content of an immersed solid dielectric material provide a relatively accurate estimate.

A further advantage of the present invention is that the method and/or device for monitoring moisture content of an immersed solid dielectric material to provide an estimate for different locations inside the transformer.

Yet another advantage of the present invention is that the device for monitoring moisture content of an immersed solid dielectric material is relatively stable over time.

Still another advantage of the present invention is that the device for monitoring moisture content of an immersed solid dielectric material operates over very large temperature and pressure ranges.

Still a further advantage of the present invention is that the device for monitoring moisture content of an immersed solid dielectric material can be easily installed or retrofitted on existing transformers, at accessible locations.

Another advantage of the present invention is that the method and/or device for monitoring moisture content of an immersed solid dielectric material are not affected by the presence of contaminants within the dielectric fluid.

A further advantage of the present invention is that the method and/or device for monitoring moisture content of an immersed solid dielectric material can be adapted by the user for use in different dielectric fluids and/or for different types of solid dielectric materials.

Still another advantage of the present invention is that the method and/or device for monitoring moisture content of an immersed solid dielectric material can provide all sorts of useful information concerning the status, or health, of the transformer(s).

Furthermore, the use of moisture detectors located upstream and downstream of the oil dryer-filter used to extract water from the oil allows for continuous monitoring of the proper functioning of the oil filter; the upstream moisture detector is preferably simultaneously used for the monitoring of the moisture content in the immersed solid dielectric.

Another advantage of the present invention is that the method and/or device for monitoring operation of a fluid dryer-filter calculate the rate of water extraction as well as the total amount of water extracted from the oil since the last filter cleaning or replacement.

According to an aspect of the present invention, there is provided a device for monitoring moisture content level of a solid dielectric material inside an enclosure, the solid dielectric material being immersed in a dielectric fluid, the dielectric fluid filling the enclosure, the solid dielectric material and the dielectric fluid having a respective moisture content, the solid dielectric material and the dielectric fluid having known water solubility properties varying with temperature thereof, the device comprises:

a moisture measuring means for measuring moisture content level of the dielectric fluid;

a temperature measuring means for measuring temperature level of the dielectric fluid; and an electronic circuit means for computing the moisture content level of the solid dielectric material, the electronic circuit means being electrically connected to both the moisture measuring means and the temperature measuring means, the electronic circuit means having the known water solubility properties of the solid dielectric material and the dielectric fluid stored therein, the electronic circuit means processing the fluid moisture content level and the fluid temperature level so as to determine the solid dielectric material moisture content level.

Preferably, the electronic circuit means includes a displaying means for displaying the solid dielectric material moisture content level, the displaying means being electrically connected to the electronic circuit means.

Preferably, the device includes an operator interfacing means for an operator to interface with the electronic circuit means, the operator interfacing means being electrically connected to the electronic circuit means so as to allow the known water solubility properties of the solid dielectric material and the dielectric fluid to be provided to and stored in the electronic circuit means.

Typically, the electronic circuit means is remotely electrically connected to both the moisture measuring means and the temperature measuring means so as to allow the moisture measuring means and the temperature measuring means to be located in a generally inaccessible location.

Typically, the device includes an operator interfacing means for an operator to interface with the electronic circuit means, the operator interfacing means being electrically connected to the electronic circuit means, the electronic circuit means providing a sensor location menu through the operator interfacing means so as to allow an operator to select a specific location of both the moisture measuring means and the temperature measuring means within the enclosure, whereby the specific location affecting determination of the solid dielectric material moisture content level by the electronic circuit means.

Typically, the device includes:

a second moisture measuring means for measuring second moisture content level of the dielectric fluid, the electronic circuit means comparing the first and second dielectric fluid moisture content levels and calculating a relative difference therebetween relative to the first dielectric fluid moisture content level, the electronic circuit means displaying on the displaying means either a warning message when the relative difference is equal or larger than a predetermined value or the first solid dielectric material moisture content level when the relative difference is smaller than the predetermined value;

whereby the second moisture measuring means being a reference moisture measuring means to enable detection of malfunction of the device.

Preferably, the predetermined value is within the range of between fifteen (15) and twenty-five (25) percent, and most preferably is twenty (20) percent.

Preferably, the moisture measuring means is a capacitance-type moisture sensor.

Alternatively, the enclosure is in fluid communication with a dielectric fluid filter unit, the filter unit defining a filter unit inlet, a filter unit outlet and a filter therebetween, the moisture measuring means and the temperature measuring means being located at the filter unit inlet, the device further comprising a second moisture measuring means located at the filter unit outlet for measuring a second moisture content level of the dielectric fluid;

the electronic circuit comparing the first and second dielectric fluid moisture content levels and calculating a filter relative difference therebetween relative to the first dielectric fluid moisture content level, the electronic circuit means displaying on the displaying means either a filter warning message when the filter relative difference is equal or smaller than a filter predetermined value or the first solid dielectric material moisture content level when the filter relative difference is larger than the filter predetermined value;

whereby the second moisture measuring means being a filter saturation reference moisture measuring means to enable detection of saturation state of the filter of the filter unit.

According to another aspect of the present invention, there is provided a method for monitoring moisture content level of a solid dielectric material inside an enclosure, the solid dielectric material being immersed in a dielectric fluid, the dielectric fluid filling the enclosure, the solid dielectric material and the dielectric fluid having a respective moisture content, the solid dielectric material and the dielectric fluid having known water solubility properties varying with temperature thereof, the method comprises the following steps:

a) measuring moisture content level of the dielectric fluid using a moisture detector;

b) measuring temperature level of the dielectric fluid using a temperature detector; and c) computing the solid dielectric material moisture content level using a processor electronic circuit, the electronic circuit being electrically connected to both the moisture detector and the temperature detector, the electronic circuit having the known water solubility properties of the solid dielectric material and the dielectric fluid stored therein, the electronic circuit processing the fluid moisture content level and the fluid temperature level so as to determine the solid dielectric material moisture content level.

Preferably, step a) includes measuring a second moisture content level of the dielectric fluid using a second moisture detector; step c) includes the electronic circuit comparing the first and second dielectric fluid moisture content levels and calculating a relative difference therebetween relative to the first dielectric, fluid moisture content level; and step d) includes displaying on the display either a warning message when the relative difference is equal or larger than a predetermined value or the first solid dielectric material moisture content level when the relative difference is smaller than the predetermined value; whereby the second moisture detector being a reference moisture detector to enable detection of malfunction of the device.

Other objects and advantages of the present invention will become apparent from a careful reading of the detailed description provided herein, within appropriate reference to the accompanying drawings.

BRIEF DESCRIPTION OF THE DRAWINGS

In the annexed drawings, like reference characters indicate like elements throughout.

DETAILED DESCRIPTION OF THE PREFERRED EMBODIMENTS

With reference to the annexed drawings the preferred embodiments of the present invention will be herein described for indicative purpose and by no means as of limitation.

Figure 1:
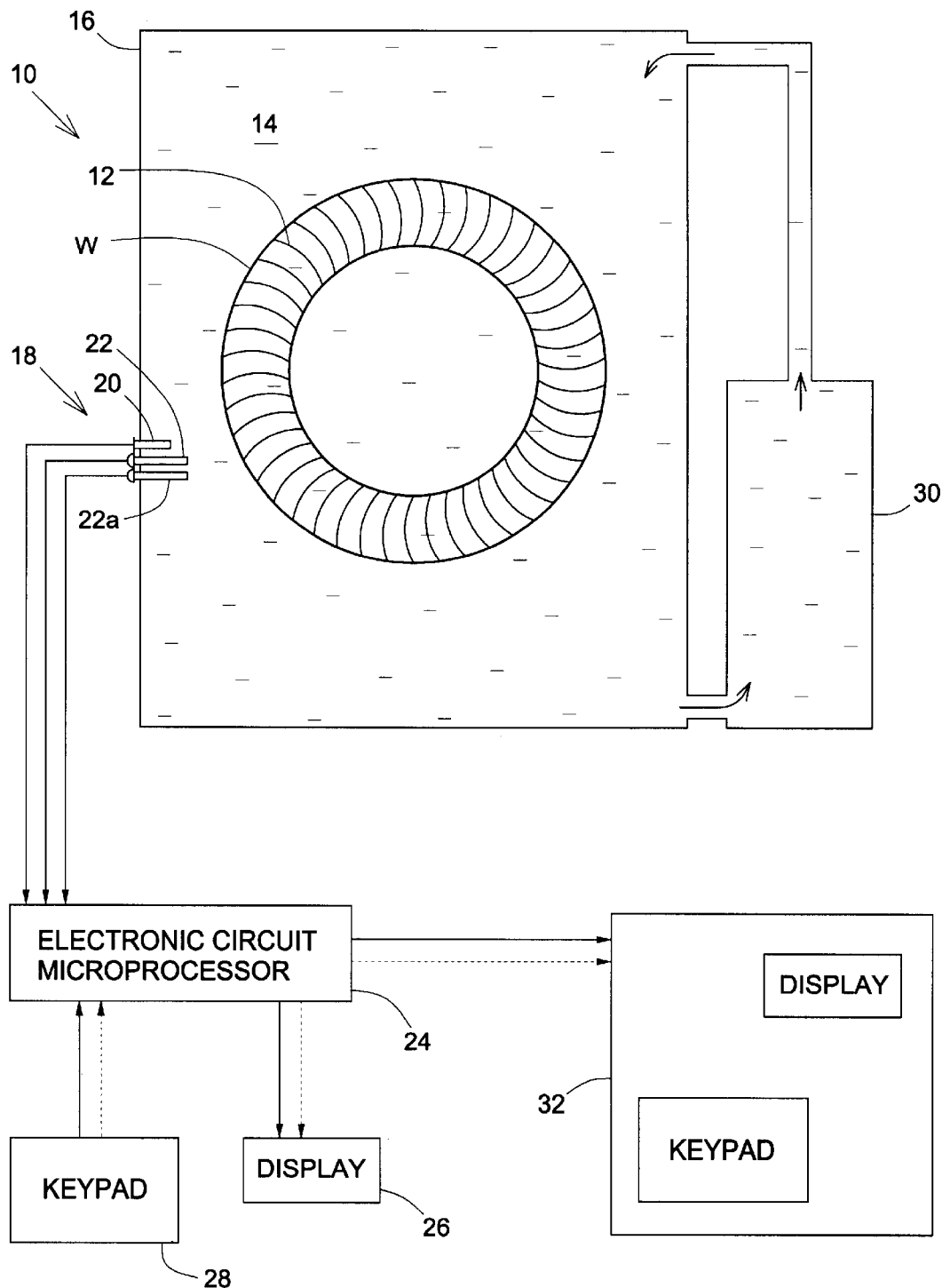
FIG. 1 is a schematic diagram illustrating a device for monitoring the moisture content of an immersed solid dielectric material in accordance with an embodiment of the present invention, the solid dielectric material of the illustration being the insulation paper used in a high power transformer.

Referring to FIG. 1, there is shown a schematic diagram of a device 10 for monitoring moisture content of a solid dielectric material 12 immersed in a dielectric fluid 14 in accordance with an embodiment of the present invention, inside an enclosure 16. The dielectric fluid 14 generally entirely submerges the solid dielectric material 12. The solid dielectric material 12 and the dielectric fluid 14 have a respective moisture content, and each has known water solubility properties varying with their respective temperature. Although the following description, schematically illustrated in FIG. 1, is generally focused on the solid dielectric material being the insulation paper 12 used to insulate the windings W of high voltage transformers immersed in oil 14, any other similar application could alternatively be considered without departing from the scope of the present invention. A representative alternate application is the insulation paper wrapped around high power transmission cables sealed immersed in oil and generally running under water and/or under ground.

The device 10 includes a probe 18 preferably comprising an oil temperature measuring means, or detector 20, and a first and a second oil moisture measuring means, or detector 22, 22a to measure the temperature level and first and second moisture content levels of the oil 14 of the transformer, respectively. The second oil moisture detector 22a is mainly used as a validation detector as explained hereinafter.

Preferably, the moisture detectors 22, 22a are capacitance-type moisture sensors well known in the art since they are substantially relatively stable over time (years), not affected by the presence of contaminants within the dielectric fluid 14 and operate over very large temperature and pressure ranges. Obviously, any other type of moisture sensor/detector could be used without departing from the scope of the present invention.

An electronic circuit means, preferably a microprocessor 24 or the like digital processor, is electrically connected to the moisture detectors 22, 22a and the temperature detector 20. The microprocessor 24 has the known water solubility properties of both the paper 12 and the oil 14 stored therein.

Also, the microprocessor is electrically connected to a displaying means, or display 26 of any conventional type, to display any information and/or data useful to the operator or user.

Before calculating the paper moisture level, the microprocessor 24 compares the first and second oil moisture content levels to determine a relative difference between the two, with respect to the first moisture content level. This relative difference is then compared to a predetermined value set at a reasonable level above which a recalibration of the moisture content detectors 22, 22a might be required due to a divergence of their performances, thereby enabling the detection of possible malfunction of the device 10. The predetermined value is preferably set within the range varying between fifteen (15) and twenty-five (25) percent, preferably at twenty (20) percent.

Accordingly, the microprocessor 24 displays either a warning message or the like on the display 26 when the above calculated relative difference is equal or larger than the predetermined value or the paper moisture content level when the calculated relative difference is smaller than the predetermined value. Obviously, other data such as the first oil moisture content level could also be provided on the display 26. The calculated paper moisture content level is determined by the microprocessor 24 that processes both the first oil moisture content level of the first moisture detector 22 and the oil temperature level of the temperature detector 20 according to an algorithm that preferably takes into account of the location of the sensing probe 18 within the transformer along with the physical characteristics (windings, dimensions, power capacity, etc.), of the transformer and the power losses of the transformer.

Although not required, the device 10 preferably includes an operator interfacing means, or keypad 28 and the like, for an operator to interface with the microprocessor 24. The keypad 28, electrically connected to the microprocessor 24, can for example allow the operator to select the specific dielectric fluid among a fluid selection menu provided by the microprocessor 24 on the display 26 (preferably provided with the keypad 28), the water solubility properties of each fluid being already stored into the microprocessor 24, or any conventional peripheral component connected thereto. Alternatively, the operator could select a new fluid and provide its water solubility properties to the microprocessor 24 via the keypad 28.

Similarly, a solid material selection menu could be considered for the different most widely used insulation papers.

Furthermore, it is well known in the art of high voltage transformers that the temperature and the moisture content of the oil 14 vary with its location within the transformer. Accordingly, the microprocessor 24 could also provide a probe location menu through the display 26 so as to allow an operator to select a specific location of the probe 18 containing the moisture detectors 22, 22a and the temperature detector 20 within the enclosure 16 via the keypad 28; the specific location obviously affecting the determination of the solid dielectric material moisture content level by the microprocessor 24.

Figure 3:
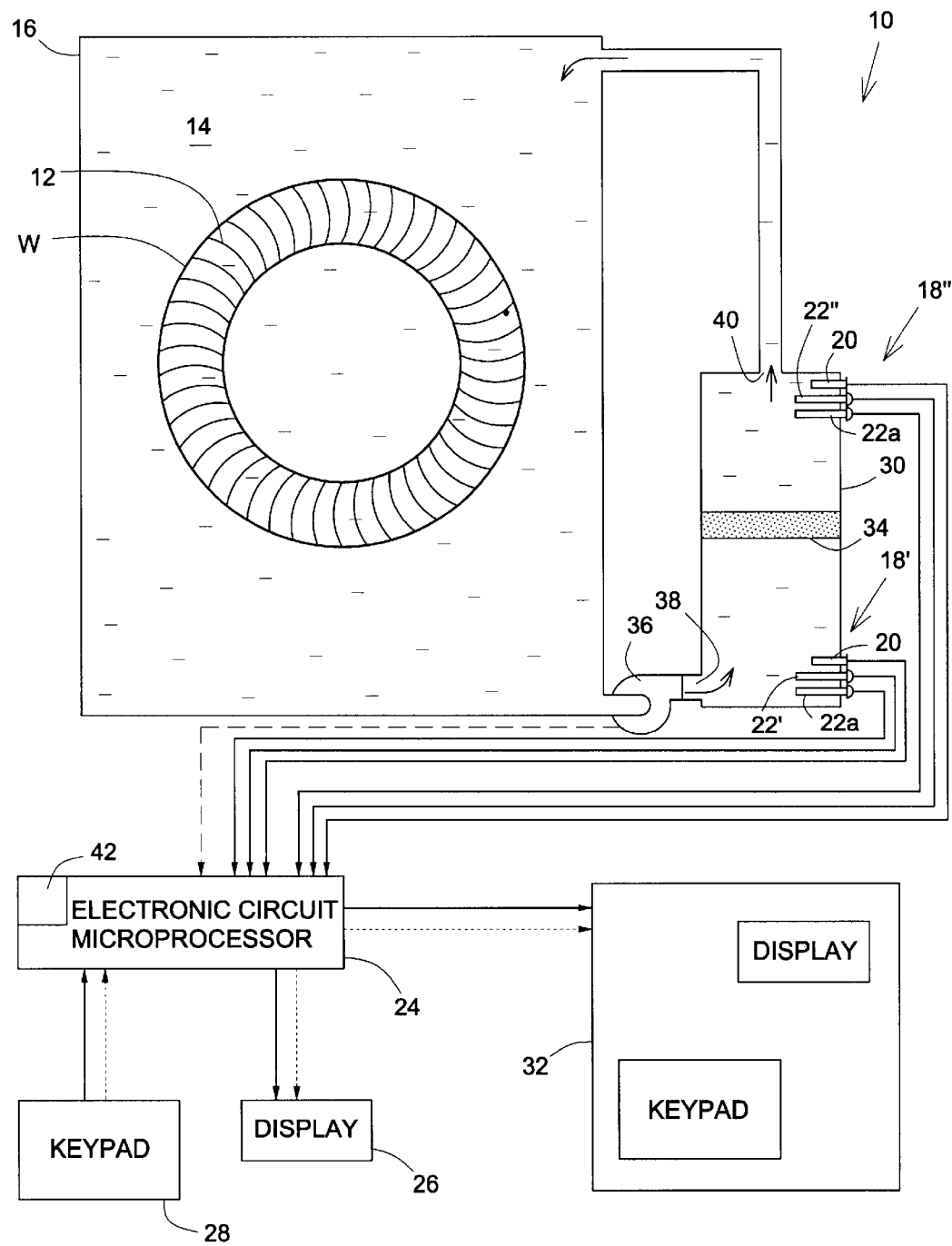
FIG. 3 is a diagram similar to FIG. 1, illustrating other locations for the moisture detectors of the embodiment of FIG. 1, upstream and downstream of an oil dryer-filter unit fluidly connected to the high power transformer.

Depending on the specific location of the probe 18, more that one probe 18', 18" connected to a same microprocessor 24 can be preferred, as illustrated in FIG. 3 by the alternate probes 18', 18" located at both the inlet 38 (upstream) and the outlet 40 (downstream) of an oil filtering unit 30 used to dry and clean the oil 14 of the transformer.

Although only the inlet alternate probe 18' is sufficient for the determination of the paper moisture content level, the outlet alternate probe 18" is used to simultaneously monitor the operation and assess the saturation state of an oil dryer-filter 34, or functioning state of any type of water extraction apparatus, located between the filtering unit inlet 38 and outlet 40. Accordingly, two generally identical oil moisture content levels detected from both probes 18', 18", or water concentrations calculated therefrom, within a filter predetermined value of about between two (2) and fifteen (15) percent, and more preferably five percent (5%), when relatively compared to each other by the microprocessor 24, indicate that the oil filter 34 is saturated, or malfunctioning, since no change occurred to the oil flowing through the filter 34 (no more detectable drying-filtering action). It is important to note that the water concentration is calculated from the measured moisture content level and the measured temperature level.

Alternatively, two moisture content levels from both probes 18', 18" slightly differing from each other, beyond preferably five percent (5%), indicate that the oil filter 34 is not saturated yet, or properly functioning, since some detectable oil drying-filtering action occurred to the oil 14 between the two probes 18', 18". It is obvious that the smaller the filter predetermined value is the more accurate the assessment is, as long as the measurement accuracy of the moisture detectors 22', 22" of the probes 18', 18" permits such a smaller filter predetermined value. This is also an important factor that the oil filter 34 be active and properly operating to increase the life duration of the transformer and maintain its overload capacity.

Typically the dryer-filter 34, or the filter unit 30, includes a fluid flowrate measuring means, preferably a volumetric pump 36 located upstream of the dryer-filter 34, for measuring the flowrate of the oil 14 flowing through the dryer-filter 34. Obviously, any other type of fluid flow meter, either built-in the filter 34 or not, could be used without departing from the scope of the present invention. As shown in long dashed lines in FIG. 3, the pump 36 is electrically connected to the microprocessor 24 for the latter to calculate a water extracting rate of the dryer-filter 34 using the flowrate of the pump 36 with the upstream and downstream moisture content levels and temperature levels measured by the moisture detectors 22', 22" and the temperature detectors 20, so as to allow an assessment of the operation of the dryer-filter 34 by the device 10.

Preferably, the microprocessor 24 includes a time register 42 which is reset to zero (0) upon cleaning or replacement of the dryer-filter 34. The microprocessor 24 computes a total amount of water extraction since the reset of the time register 42 (or last maintenance/replacement of the dryer-filter 34) from the calculated water extracting rate of the dryer-filter 34.

Any information calculated or nor, such the filter warning message, the water extracting rate and/or the total amount of water extraction can be displayed on the display 26.

The microprocessor 24 typically provides a dryer-filter menu through the operator interfacing means so as to allow the operator to enter a water extraction capacity of the dryer-filter 34 and a flowrate associated with the pump 36 or the like to the microprocessor 24 through the keypad 28. Consequently, the microprocessor 24 compares the calculated total amount of water extraction to the water extraction capacity in order to provide an assessment of the operation of the dryer-filter 34 by providing the operator with a general remaining time on the display 26 before the next cleaning or replacement of the dryer-filter 34 is required.

As it would be obvious to one skilled in the art, the microprocessor 24 can be electrically connected to a remote unit 32 such as a conventional main computer, a handheld computer, laptop computer or the like, preferably having its own display and keypad, used to post-process the data (oil moisture content level, oil temperature level and/or paper moisture content level) obtained from at least one probe 18 connected to one or more microprocessor circuits 24, from a same or different transformers. Post-processing includes here any type of conventional post-processing form and/or further algorithmic calculation, usually time-consuming, to determine real-time overload capacity of the transformer(s) from evaluation of paper moisture content levels at different critical areas of the transformer(s).

The probes 18 of the device 10 of the present invention can be either installed during manufacturing of the transformers or retrofitted in existing transformers. Accordingly, the location of these probes 18 could eventually be relatively inaccessible to an operator. Therefore, all electrical connections described hereinabove between the different components could be remote or wireless type connections without departing from the scope of the present invention, as illustrated in short dashed lines in FIGS. 1 and 3, although the physical electrical links are preferred for reliability purposes.

Figure 2:
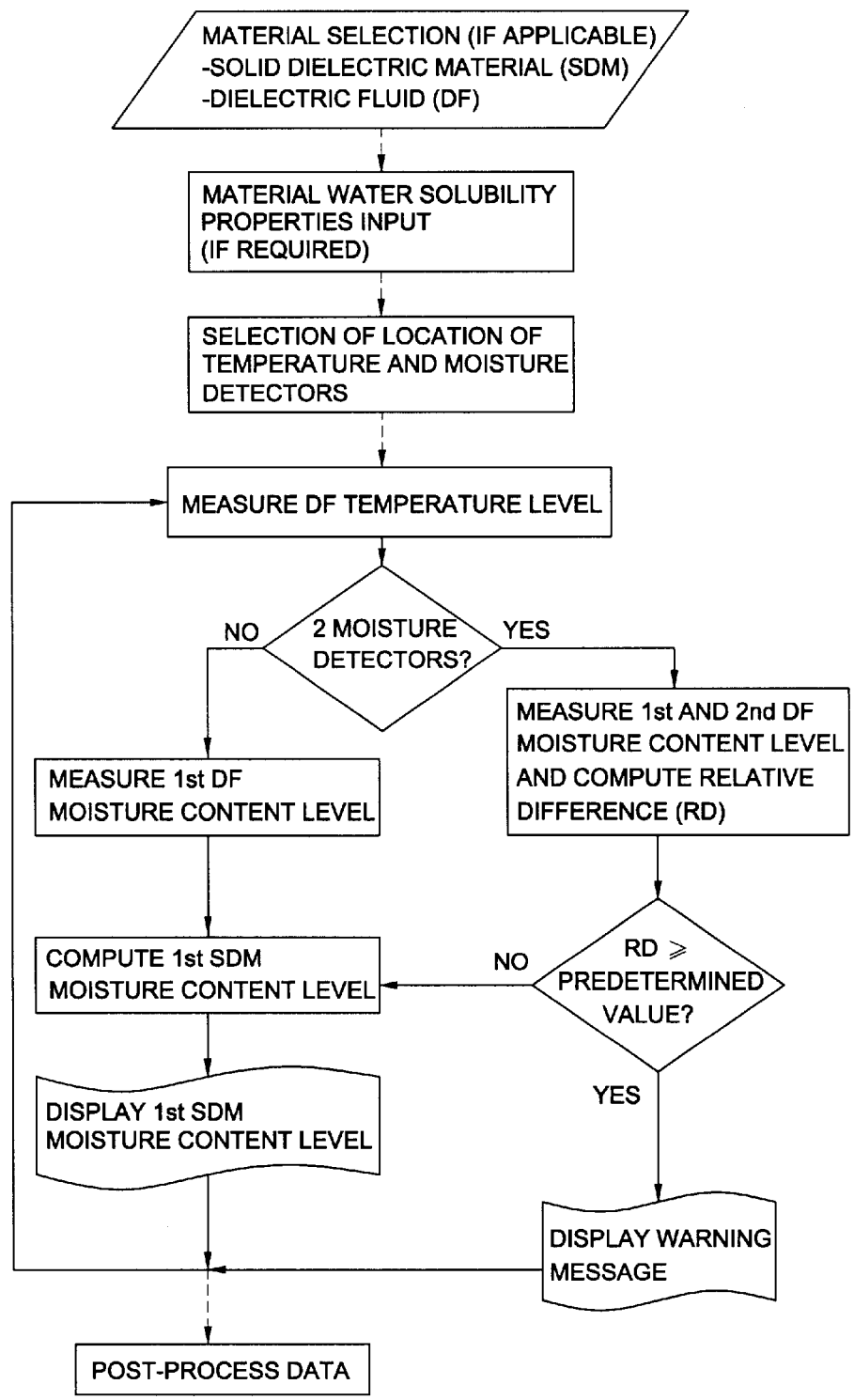
FIG. 2 is a schematic flow diagram showing a method for monitoring the moisture content of an immersed solid dielectric material in accordance with an embodiment of the present invention.

The present invention also refers to a method for monitoring moisture content of a solid dielectric material 12 immersed in a dielectric fluid 14, as schematically represented by the flow diagram of FIG. 2. The method comprises the following steps of:

a) measuring moisture content level of the dielectric fluid, or oil 14, using a moisture detector 22;

b) measuring temperature level of the oil 14 using a temperature detector 20; and c) computing the solid dielectric material moisture level using an electronic circuit or microprocessor 24, the latter being electrically connected to both the moisture detector 22 and the temperature detector 20.

The method preferably includes the step of:

d) displaying the solid dielectric material moisture content level using the display 26.

In the method, the step a) could include the measurement of a second moisture content level of the oil 14 using a second moisture detector 22a. Step c) includes the comparison of the first and second dielectric fluid moisture content levels and the calculation of a relative difference there between, relative to the first dielectric fluid moisture content level. And the following step:

d) displaying on the display 26 either a warning message when the relative difference is equal or larger than the predetermined value hereinabove described or the first solid dielectric material moisture content level when the relative difference is smaller than the predetermined value.

Alternatively, as illustrated by dashed connecting lines in FIG. 2, the method could include the step of:

d) sending the solid dielectric material moisture level to a remote unit 32, such as a micro-computer, a handheld computer or the like, so as to allow post-processing thereof; the computer device is electrically connected to the microprocessor.

Optionally, the method includes after step b) the step of:

b1) providing an operator interface or keypad 28 so as to allow the operator to interface with the microprocessor 24, possibly via a remote unit or handheld computer 32 connected thereto, and either perform a selection of the paper material 12 and/or oil 14 among a material selection menu provided by the microprocessor 24 on the display 26 or enter the known water solubility properties of a new paper material 12 and/or oil 14 present in the transformer.

Similarly, step b1) could allow an operator to select a specific location of the probe 18 within the enclosure 16 among a detector location menu provided by the microprocessor 24 on the display 26 through the keypad 28.

As illustrated in FIG. 3, when the probe 18' is located upstream of the dryer-filter 34, it could simultaneously be used, in conjunction with a second probe 18" located downstream of the dryer-filter 34, to monitor the operation of the latter.

Figure 4:
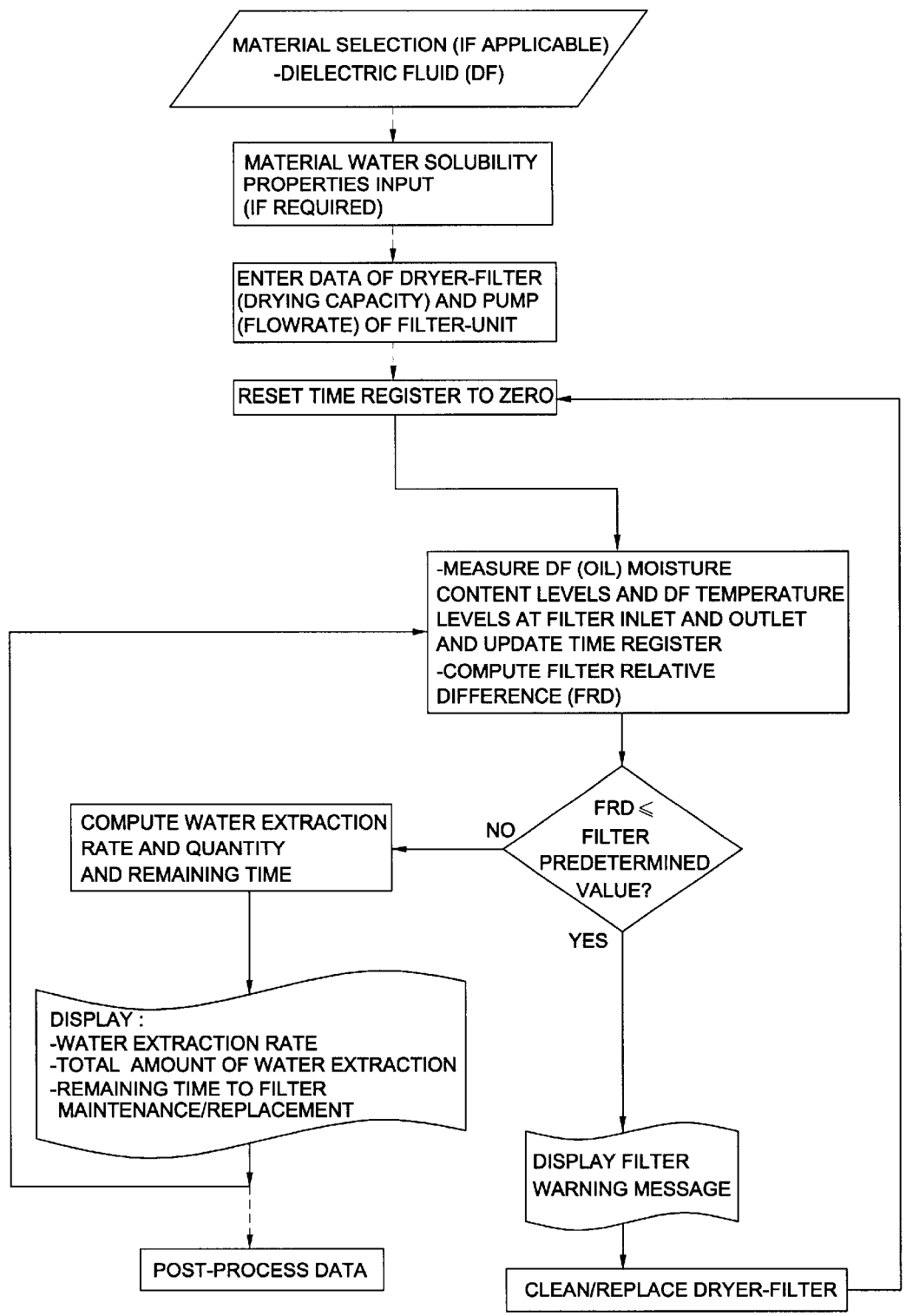
FIG. 4 is a schematic flow diagram showing the monitoring of the functioning of the oil dryer-filter unit of FIG. 3.

Accordingly, as illustrated in the schematic flow diagram of FIG. 4, the method for monitoring the operation of the oil dryer-filter 34 comprises the following steps of:

measuring a first inlet moisture content level of the oil 14 upstream of the oil dryer-filter 34 using an inlet moisture detector 22';

measuring a second outlet moisture content level of the oil 14 downstream of the oil dryer-filter 34 an outlet moisture detector 22"; and computing a filter relative difference between the first and second dielectric fluid moisture content levels relative to the first dielectric fluid moisture content level using a microprocessor 24. The latter is electrically connected to both first and second moisture detectors 22', 22" and provides a filter warning message when the filter relative difference is equal or smaller than a filter predetermined value;

whereby the method enables detection of saturation or malfunctioning state of the dryer-filter 34.

Optionally, the dryer-filter 34 includes a fluid flowrate measuring means, or volumetric pump 36, electrically connected to the microprocessor 24 to measure the flowrate of oil 14 flowing through the dryer-filter 34, and the method further includes the step of:

measuring a first temperature level of the oil 14 upstream of the fluid dryer-filter 34 using a first temperature detector 20;

measuring a second temperature level of the oil 14 downstream of the fluid dryer-filter 34 using a second temperature detector 20;

computing a water extracting rate of the dryer-filter 34 with the microprocessor 24 using the flowrate of the oil 14, the first and second moisture content levels and the first and second temperature levels, the microprocessor 24 being electrically connected to the pump 36 and the first and second temperature detectors 20; whereby the method allows for assessment of the operation of the dryer-filter 34.

Also, the microprocessor 24 includes a time register 42, and the method further includes the steps of:

resetting the time register 42 to zero (0) upon cleaning or replacement of the dryer-filter 34; and computing a total amount of water extraction since resetting of the time register 42 from the water extracting rate of the dryer-filter 34.

Typically, the method includes the step of providing an operator interface, or keyboard 28/display 26, electrically connected to the microprocessor 24 for an operator to interface therewith. The microprocessor 24 provides a dryer-filter menu through the display 26 so as to allow an operator to provide the microprocessor 24 with a water extraction capacity of the dryer-filter 34 and a flowrate of the pump 36. The microprocessor 24 compares the total amount of water extraction to the water extraction capacity to determine assessment of the proper operation of the dryer-filter 34 and to provide the operator with a general remaining time on the display 26 before a next cleaning or replacement of the dryer-filter 34 is required.

The above description always refers to the first oil moisture content level being used in the calculation of the paper moisture content level when two moisture detectors 22, 22a are present in the probe 18, but the second oil moisture content level, or either an average of the two, can be used in the calculation of the paper moisture content level without departing from the scope of the present invention.

Although not specified hereinabove, the device 10 preferably continuously monitors the paper moisture content level, many times per seconds, any monitoring rate could be considered depending on the specific need of the operator and without departing from the scope of the present invention.

Although the present device for monitoring moisture content of an immersed solid dielectric material has been described with a certain degree of particularity, it is to be understood that the disclosure has been made by way of example only and that the present invention is not limited to the features of the embodiments described and illustrated herein, but includes all variations and modifications within the scope and spirit of the invention as hereinafter claimed.

I claim:

1. A device for monitoring moisture content level of a solid dielectric material inside an enclosure, said solid dielectric material being immersed in a dielectric fluid, said dielectric fluid filling said enclosure, said solid dielectric material and said dielectric fluid having a respective moisture content, said solid dielectric material and said dielectric fluid having known water solubility properties varying with temperature thereof, said device comprising:

a moisture measuring means for measuring moisture content level of said dielectric fluid;

a temperature measuring means for measuring temperature level of said dielectric fluid; and an electronic circuit means for computing said moisture content level of said solid dielectric material, said electronic circuit means being electrically connected to both said moisture measuring means and said temperature measuring means, said electronic circuit means having said known water solubility properties of said solid dielectric material and said dielectric fluid stored therein, said electronic circuit means processing said fluid moisture content level and said fluid temperature level so as to determine said solid dielectric material moisture content level.

2. The device of claim 1, wherein said electronic circuit means includes a displaying means for displaying said solid dielectric material moisture content level, said displaying means being electrically connected to said electronic circuit means.

3. The device of claim 1, including an operator interfacing means for an operator to interface with said electronic circuit means, said operator interfacing means being electrically connected to said electronic circuit means so as to allow said known water solubility properties of said solid dielectric material and said dielectric fluid to be provided to and stored in said electronic circuit means.

4. The device of claim 1, wherein said electronic circuit means is remotely electrically connected to both said moisture measuring means and said temperature measuring means so as to allow said moisture measuring means and said temperature measuring means to be located in a generally inaccessible location.

5. The device of claim 1, including an operator interfacing means for an operator to interface with said electronic circuit means, said operator interfacing means being electrically connected to said electronic circuit means, said electronic circuit means providing a sensor location menu through said operator interfacing means so as to allow an operator to select a specific location of both said moisture measuring means and said temperature measuring means within said enclosure, whereby said specific location affecting determination of said solid dielectric material moisture content level by said electronic circuit means.

6. The device of claim 2, including:
   a second moisture measuring means for measuring second moisture content level of said dielectric fluid, said electronic circuit means comparing said first and second dielectric fluid moisture content levels and calculating a relative difference therebetween relative to said first dielectric fluid moisture content level, said electronic circuit means displaying on said displaying means either a warning message when said relative difference is equal or larger than a predetermined value or said first solid dielectric material moisture content level when said relative difference is smaller than said predetermined value;
   whereby said second moisture measuring means being a reference moisture measuring means to enable detection of malfunction of said device.

7. The device of claim 6, wherein said predetermined value is within the range of between fifteen (15) and twenty-five (25) percent.

8. The device of claim 7, wherein said predetermined value is generally twenty (20) percent.

9. The device of claim 1, wherein said moisture measuring means is a capacitance-type moisture sensor.

10. A method for monitoring moisture content level of a solid dielectric material inside an enclosure, said solid dielectric material being immersed in a dielectric fluid, said dielectric fluid filling said enclosure, said solid dielectric material and said dielectric fluid having a respective moisture content, said solid dielectric material and said dielectric fluid having known water solubility properties varying with temperature thereof, said method comprising the following steps:
   a) measuring moisture content level of said dielectric fluid using a moisture detector;
   b) measuring temperature level of said dielectric fluid using a temperature detector; and
   c) computing said solid dielectric material moisture content level using a processor electronic circuit, said electronic circuit being electrically connected to both said moisture detector and said temperature detector, said electronic circuit having said known water solubility properties of said solid dielectric material and said dielectric fluid stored therein, said electronic circuit processing said fluid moisture content level and said fluid temperature level so as to determine said solid dielectric material moisture content level.

11. The method recited in claim 10, including the step of:
   d) displaying said solid dielectric material moisture level using a display, said display being electrically connected to said electronic circuit to receive said solid dielectric material moisture content level therefrom.

12. The method recited in claim 11, wherein said display is remotely electrically connected to said electronic circuit.

13. The method recited in claim 11, wherein step a) includes measuring a second moisture content level of said dielectric fluid using a second moisture detector; step c) includes said electronic circuit comparing said first and second dielectric fluid moisture content levels and calculating a relative difference therebetween relative to said first dielectric fluid moisture content level; and step d) includes displaying on said display either a warning message when said relative difference is equal or larger than a predetermined value or said first solid dielectric material moisture content level when said relative difference is smaller than said predetermined value; whereby said second moisture detector being a reference moisture detector to enable detection of malfunction of said device.

14. The method recited in claim 13, wherein said predetermined value is within the range of between fifteen (15) and twenty-five (25) percent.

15. The method recited in claim 14, wherein said predetermined value is generally twenty (20) percent.

16. The method recited in claim 10, including the step of:
   d) sending said solid dielectric material moisture content level to a remote unit so as to allow post-processing thereof, said remote unit being electrically connected to said electronic circuit.

17. The method recited in claim 10, including after step b) the step of:
   b1) providing an operator interface so as to allow said known water solubility properties of said solid dielectric material and said dielectric fluid to be provided therethrough; said operator interface being electrically connected to an electronic circuit for an operator to interface therewith and store said known water solubility properties of said solid dielectric material and said dielectric fluid therein.

18. The method recited in claim 17, wherein said operator interface is remotely electrically connected to said electronic circuit.

19. The method recited in claim 10, including after step b) the step of:
   b1) providing an operator interface electrically connected to an electronic circuit for an operator to interface therewith, said electronic circuit providing a detector location menu through said operator interface so as to allow an operator to select a specific location of both said moisture detector and said temperature detector, within said enclosure, whereby said specific location affecting determination of said solid dielectric material moisture content level by said electronic circuit.

20. The method recited in claim 10, wherein said moisture detector is a capacitance-type moisture sensor.

* * * * *